United States Patent
Nzike et al.

(10) Patent No.: US 10,519,946 B2
(45) Date of Patent: Dec. 31, 2019

(54) PERISTALTIC PUMP AND METHOD OF TRANSPORTING MATERIAL WITH A PERISTALTIC PUMP

(71) Applicant: Sanofi-Aventis Deutschland GmbH, Frankfurt am Main (DE)

(72) Inventors: Philippe Nzike, Frankfurt am Main (DE); Michael Schabbach, Frankfurt am Main (DE); Olaf Zeckai, Weinheim (DE); Meinolf Werner, Worms (DE); Ole Simonowsky, Blankenrath (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 43 days.

(21) Appl. No.: 14/342,278

(22) PCT Filed: Sep. 21, 2012

(86) PCT No.: PCT/EP2012/068697
§ 371 (c)(1),
(2) Date: Feb. 28, 2014

(87) PCT Pub. No.: WO2013/041703
PCT Pub. Date: Mar. 28, 2013

(65) Prior Publication Data
US 2014/0356193 A1    Dec. 4, 2014

(30) Foreign Application Priority Data

Sep. 21, 2011 (EP) .................................. 11182230

(51) Int. Cl.
*F04B 43/12* (2006.01)
*F04B 43/09* (2006.01)
(Continued)

(52) U.S. Cl.
CPC ............ *F04B 43/12* (2013.01); *F04B 43/082* (2013.01); *F04B 43/095* (2013.01);
(Continued)

(58) Field of Classification Search
CPC ...... F04B 43/12; F04B 43/082; F04B 43/095; F04B 17/003; F04B 43/04; F04B 43/046;
(Continued)

(56) References Cited

U.S. PATENT DOCUMENTS 1,874,667 A * 8/1932 Yoshinobu Wada ........................
                                              A61M 1/1037
                                                   222/209
2,483,924 A * 10/1949 Jean Moulinier ..... A61M 5/142
                                                   210/416.1
(Continued)

FOREIGN PATENT DOCUMENTS

DE    19729612 A1 *  1/1999  ............ F04B 43/082
DE    10246469 A1    4/2004
(Continued)

OTHER PUBLICATIONS

English Translation of DE 19729612 A1 dated Feb. 23, 2017.*
(Continued)

*Primary Examiner* — Dominick L Plakkoottam
*Assistant Examiner* — Connor J Tremarche
(74) *Attorney, Agent, or Firm* — McCarter & English, LLP (57) ABSTRACT

A peristaltic pump comprises a tube to transport a material in a transport direction and one or more piezoelements, which are configured to cause a squeezing of the tube. Furthermore, a method of transporting material comprises the step of successively actuating the piezoelements along the transport direction of the material and thereby causing a squeezing of the tube.

28 Claims, 5 Drawing Sheets

(51) Int. Cl.
  *F04B 43/08* (2006.01)
  *F04B 45/08* (2006.01)
  *F04B 17/00* (2006.01)
(52) U.S. Cl.
  CPC . *F04B 43/1223* (2013.01); *A61M 2205/0294* (2013.01); *F04B 17/003* (2013.01); *F04B 43/08* (2013.01); *F04B 43/09* (2013.01); *F04B 45/08* (2013.01)
(58) Field of Classification Search
  CPC ........ F04B 43/021; F04B 43/08; F04B 43/09; F04B 43/1223; F04B 45/08; A61M 1/1058; A61M 2205/0294
  USPC ................................ 417/412, 413.2
  See application file for complete search history.

(56) References Cited

U.S. PATENT DOCUMENTS

| | | | | |
|---|---|---|---|---|
| 3,679,331 | A * | 7/1972 | Kushner | F04B 43/086 222/214 |
| 4,014,318 | A * | 3/1977 | Dockum | A61M 1/1053 137/527 |
| 4,443,216 | A * | 4/1984 | Chappell | A61M 5/142 128/DIG. 12 |
| 4,479,797 | A * | 10/1984 | Kobayashi | A61M 5/14228 417/474 |
| 4,537,561 | A * | 8/1985 | Xanthopoulos | A61M 5/142 128/DIG. 12 |
| 4,950,245 | A * | 8/1990 | Brown | A61M 5/14228 128/DIG. 12 |
| 5,074,844 | A * | 12/1991 | Zdeb | A61M 5/1409 604/83 |
| 5,083,908 | A | 1/1992 | Gagnebin et al. | |
| 5,094,429 | A * | 3/1992 | Dostert | F02M 51/0603 239/102.2 |
| 5,152,680 | A * | 10/1992 | Okada | F04B 43/082 417/474 |
| 5,494,415 | A | 2/1996 | Morita | |
| 5,938,413 | A * | 8/1999 | Makino | F04B 43/082 417/474 |
| 5,988,983 | A | 11/1999 | Furusawa | |
| 6,279,871 | B1 * | 8/2001 | Ogura | F16K 31/007 251/129.06 |
| 6,551,298 | B1 | 4/2003 | Zhang et al. | |
| 7,432,637 | B2 * | 10/2008 | Ogawa | F04B 17/003 310/328 |
| 2004/0234401 | A1 * | 11/2004 | Banister | F04B 43/043 417/474 |
| 2006/0110274 | A1 * | 5/2006 | Gottschalk | F04B 43/082 417/477.6 |
| 2007/0154336 | A1 | 7/2007 | Miyazaki et al. | |
| 2009/0107902 | A1 * | 4/2009 | Childers | A61M 1/16 210/196 |
| 2010/0111733 | A1 * | 5/2010 | Ramunas | F04B 43/123 417/474 |

FOREIGN PATENT DOCUMENTS

| | | |
|---|---|---|
| DE | 102009051806 A1 | 5/2011 |
| GB | 2238833 A | 6/1991 |
| JP | S59-162381 A | 9/1984 |
| JP | H02-4382 A | 1/1990 |
| JP | H04-105983 A | 4/1992 |
| JP | H05-195958 A | 8/1993 |
| JP | H09-151856 A | 6/1997 |
| JP | 3107585 U | 2/2005 |
| JP | 2007-61389 A | 3/2007 |
| JP | 2007061389 A * | 3/2007 |
| JP | 2007-0154336 A | 6/2007 |
| JP | 2007275548 A | 10/2007 |
| JP | 2008-054492 A | 3/2008 |
| WO | 03027503 A1 | 4/2003 |
| WO | 2004071684 A1 | 8/2004 |

OTHER PUBLICATIONS

English Translation of JP-2007061389-A dated Sep. 11, 2018 (Year: 2018).*
English Translation of Japanese Patent Application No. JPS06-008371.
English Translation of Abstract of Japanese Patent Application No. JP H05-195958.
English Translation of Notice of Reasons for Rejection issued in Japanese Patent Application No. 2014-531253 dated Jul. 5, 2016.

* cited by examiner

PERISTALTIC PUMP AND METHOD OF TRANSPORTING MATERIAL WITH A PERISTALTIC PUMP

CROSS REFERENCE TO RELATED APPLICATIONS

The present application is a U.S. National Phase application pursuant to 35 U.S.C. § 371 of International Application No. PCT/EP2012/068697 filed Sep. 21, 2012, which claims priority to European Patent Application No. 11182230.0 filed Sep. 21, 2011. The entire disclosure contents of these applications are herewith incorporated by reference into the present application.

FIELD OF INVENTION

The present disclosure relates to a peristaltic pump.

BACKGROUND

Peristaltic pumps are configured to transport a material in a tube by squeezing the tube.

Peristaltic pumps are known from the prior art, as for example from the documents DE 10246469 A1 or DE 19729612 A1.

It is an object of the present invention to provide a peristaltic pump, which shows improved properties.

Furthermore, it is an object of the invention to provide an improved method for transporting material with a peristaltic pump.

SUMMARY

According to one aspect of the present disclosure, a peristaltic pump is provided, comprising a tube and one or more piezoelements. Preferably, the pump comprises a plurality of piezoelements. The tube is configured to transport a material in a transport direction. The piezoelements are configured to cause a squeezing of the tube.

Preferably, the piezoelements cause a squeezing of the tube when they are actuated by applying a voltage. Preferably, the piezoelements are caused to expand when they are actuated. When the piezoelements are discharged, they may contract again to their uncharged size.

The peristaltic pump may be configured such that a contraction of at least one of the piezoelements enables a widening of the tube.

The peristaltic pump may be intended to be applied for medical use. Preferably, the peristaltic pump is configured to transport medical fluids. Preferably, the peristaltic pump is configured to dispense small amounts of fluids to a tissue. In particular, the pump may be used in the field of microfluidics. In a preferred embodiment, the peristaltic pump may transport highly sensitive material. The material may be a medicament, as for example insulin. As a further example, the pump may be configured as a dialysis pump to transport blood.

Preferably, the piezoelements are used as pump heads. A pump head may be an element which by its movement may cause a squeezing of the tube. Preferably, the piezoelements are electrically powered. Thus, no mechanically powered pump heads, for example camshafts, may be necessary. Thus, the peristaltic pump may contain very few mechanical components and may thereby be less prone to abrasion. A low number of mechanical components may keep the maintenance effort low. In particular, no additional valves may be necessary, since the piezoelements may serve as valves. In particular, the piezoelements may inhibit a reflow of the material in a direction opposite to the transport direction.

Preferably, the piezoelements have a short response time. Thereby, a very high dispensing speed may be allowed. Preferably, also a very low dispensing speed may be allowed. Thereby, a gentle treatment of the material transported in the tube may be possible.

The peristaltic pump of the present disclosure may have improved pump parameters. A short response time of the piezoelements may allow an accurately assessable dispensing speed, and thereby a high dosing precision may be achieved. A favourable sequence of actuating the piezoelements, for example such that at least one piezoelement is expanded at any particular time may reduce the tendency of the material to flow back. Because of the short response time, the pump may also show a high evenness of pumping, which means that the flow rate is constant. In a preferred embodiment, the peristaltic pump may be configured such that a constant and shock free pumping is possible. The constant pump capacity may as well lead to a high reproducibility of the pumping amount.

Preferably, the expanding direction of the piezoelements may run perpendicular relative to a longitudinal axis of the tube. Thereby, friction forces may be low such that a relative movement between the tube and the pump and an axial movement of the tube is inhibited.

Preferably, the piezoelements are arranged along the tube, preferably in a row along the tube. The piezoelements may be arranged with a distance to the tube when they are not actuated. In a preferred embodiment, the piezoelements can expand in only one direction, and the movement in the other direction is blocked. In a further embodiment, several piezoelements may be arranged on top of each other, thereby forming a multi-part piezo-actuator.

The piezoelements may be arranged in a holder. The holder may be configured such that a piezoelement may expand in one direction and the expansion in the opposite direction is blocked by the holder. Preferably, when a piezoelement is actuated by applying a voltage to the piezoelement, the piezoelement expands in a direction such that the distance between the tube and the piezoelement decreases.

The peristaltic pump may comprise a large number of piezoelements. A large number of piezoelements may have a positive effect on pulsation during the operation of the pump. Preferably, the peristaltic pump does not show a pulsating kind of pumping.

Preferably, the tube is arranged in a linear form along an axis. In a preferred embodiment, the tube is free from curved sections. Particularly, the tube may be configured such that it does not show a U-shaped section. Thereby a positioning of the tube in the peristaltic pump during an exchange of the tube may become easier and reproducible. Thereby, the risk of misalignment of the tube may be reduced. This may lead to a significant higher dose accuracy.

Preferably, the peristaltic pump of the present disclosure comprises at least one lever. Preferably, the lever is arranged between at least one of the piezoelements and the tube. Preferably, the peristaltic pump is configured such that a movement of the lever is caused by an expansion of at least one of the piezoelements.

Preferably, the peristaltic pump comprises a plurality of levers.

The levers may be arranged in a row. Preferably, the levers are arranged along the tube. The levers may be arranged with a distance to the tube when the piezoelements are not actuated. The levers may be arranged such that there is no gap or a gap as small as possible between the levers. Thereby, a high evenness of pumping may be achieved.

Preferably, the peristaltic pump comprises a plurality of piezoelements and a plurality of levers. Preferably, the number of piezoelements is equal to the number of levers. In a preferred embodiment, each lever is moved by one of the piezoelements.

In a preferred embodiment, at least one of the piezoelements contacts the lever in a contact area of the lever. As examples, the contact area may be point-shaped or line-shaped.

The lever may comprise two ends. The lever may be positioned such that one end of the lever may be able to contact the tube.

In a preferred embodiment, the peristaltic pump is configured such that the expansion of at least one of the piezoelements causes a rotation of the lever around a rotation axis.

The rotation axis preferably runs through one of the ends of the lever, preferably the end which is adjacent to a contact area of the lever with the piezoelement. In other embodiments, the rotation axis may lie somewhere in between the ends of the lever.

Preferably, when the piezoelement expands it contacts the lever in a contact area and applies a force on the lever. The applied force may cause the lever to fulfill a rotational movement around the rotation axis. The direction of the rotational movement of the lever is preferably such that one end of the lever moves towards the tube. Thereby, the lever may squeeze the tube and thereby diminish the cross-section of the tube. Preferably, the lever squeezes the tube until the tube is closed.

The lever may be configured to amplify the movement of the piezoelement such that a mechanical advantage is achieved, since the expansion of the piezoelement may be small compared to the diameter of the tube. Preferably, the length of the lever and the position of the rotation axis are such that the movement of the piezoelement is amplified by the lever. Thereby, the size of the piezoelements and also the size of the peristaltic pump may be kept small. Preferably, the movement of the piezoelement is amplified such that a small expansion of the piezoelement may effect a squeezing of the tube.

In a further embodiment, the peristaltic pump may be free from a lever such that the piezoelement squeezes the tube without a lever as an intermediate element. Thereby, a direct interaction between the piezoelements and the tube can be realized. Thereby, the amount of mechanical parts may be reduced.

The peristaltic pump may comprise at least one lever spring. The lever spring may be configured to pretension the lever in a direction that is opposed to the direction of movement of the lever caused by an expansion of at least one of the piezoelements.

When the piezoelement contracts, it may be possible that the lever does not withdraw from the tube completely on its own, so that the tube may not achieve its original diameter. Preferably, the original diameter of the tube is the diameter of the tube when not squeezed by the lever. By the lever spring, it may be ensured that the lever completely withdraws from the tube and the tube can achieve its original diameter. The lever spring may be, for example, a flat spring. In a further embodiment, the lever spring may be another kind of spring, for example a spiral spring. In order to withdraw the lever from the tube, the lever spring may cause a rotational movement of the lever around a rotation axis in a direction that is opposite to the moving direction of the lever caused by the expansion of a piezoelement. The movement of the lever caused by the lever spring may be stopped, when the lever abuts the contracted piezoelement at a contact area of the lever.

In a preferred embodiment, the peristaltic pump comprises a main body and an exchange part configured to be attachable to the main body.

Preferably, the main body comprises a housing and the one or more piezoelements. In a preferred embodiment, the main body comprises at least one lever and at least one lever spring.

Certain elements of the peristaltic pump may have to be exchanged after use, before the peristaltic pump is reused again. As an example, this may be required when the peristaltic pump is configured for medical use. Preferably, an exchange part makes this process simple and quick for a user.

The exchange part is preferably designed to be attached to and detached from the main body. The exchange part may be locked on the main body. Preferably, the exchange part is configured to be attached and detached to the main body in a simple manner. The exchange part may be configured to carry elements of the peristaltic pump which have to be exchanged periodically. Preferably, the elements which are carried by the exchange part are pre-assembled at the exchange part. This may make the exchange of the exchange part very simple for the user. Preferably, the exchange part is configured to be a disposable such that it can be replaced by a new, unused exchange part.

In one embodiment, it may be possible to exchange the elements of the exchange part individually, for example one needle or the tube, and reuse the remaining elements of the exchange part.

Preferably, the exchange part comprises a tube guide for guiding the tube.

A tube guide may be a guide along which or in which the tube may run. The tube may be attached to the tube guide. Preferably, by means of the tube guide, the position of the tube in the pump is determined. Preferably, the tube guide enables that an accurate insertion and adjustment of the tube is simple and quick. In a preferred embodiment, the tube is positioned between the tube guide and a lever.

Preferably, when the exchange part is detached from the main body, the tube is removed from the peristaltic pump together with the exchange part. Preferably, the tube is located in the exchange part in a way that when the exchange part is attached to the main body, the tube is positioned correctly relative to the piezoelements. For this aim, the main body may comprise positioning elements, so that the exchange part can be aligned properly.

The peristaltic pump may comprise a receptacle. The receptacle may be located in the main body of the peristaltic pump. The receptacle may contain the material to be transported, for example a liquid material, in particular a liquid medicament.

The peristaltic pump may comprise at least one needle. As an example, the exchange part may be configured to carry at least one needle.

In particular, the needle may be configured to dispense the material, for example a fluid, to a tissue. The needle may be located such that material can flow from the tube into the needle. The needle may be positioned at an end of the exchange part which is faced away from a receptacle.

Additionally or alternatively, the peristaltic pump may comprise at least one needle by which the tube is provided with new material. Preferably, the needle may be attached to the exchange part. The needle may be positioned at an end of the exchange part which is faced towards a receptacle. The needle may be configured to be inserted into the receptacle. Preferably, the needle may be connected with the tube such that material can flow from the receptacle into the tube.

In a preferred embodiment, the peristaltic pump may comprise a first and a second needle. As an example, the exchange part may be configured to carry a first and a second needle. The first needle may be configured to dispense the material and the second needle may be configured to provide the tube with new material.

In a further embodiment, the exchange part may comprise at least one screw thread for attaching and detaching an exchangeable needle. In this case, at least one of the needles may be exchanged individually.

In one embodiment the pump may be configured such that, in order to enable a detachment of the exchange part, a receptacle has to be removed from the main body first. After that, the exchange part may be enabled to be detached from the main body. The receptacle may be removed in a direction parallel to the transporting direction of the tube. When the receptacle has been removed, the exchange part may be removed in a direction perpendicular to the transporting direction of the tube. Alternatively, the exchange part may be removed in a direction parallel to the tube.

A new exchange part may be attached to the main body after the used exchange part has been detached. There may be positioning elements at the main body in order to align the exchange part correctly, and safety elements, for example snap arms, to fix the exchange part during insertion.

After replacing the exchange part, a new receptacle may be inserted into the pump. During insertion of the receptacle a needle may be pierced into the receptacle.

In a further embodiment, the pump may be configured such that, in order to enable a detachment of the exchange part, the receptacle may not have to be removed. In this embodiment, a needle attached to the exchange part may be pierced into, respectively pulled out of the receptacle while the exchange part is replaced. In this embodiment, both components, namely the exchange part and the receptacle may be designed such that their moving directions during their detachment from the main body are parallel to each other. In this case the sequence of replacement of receptacle and exchange part may be unimportant, since the exchange part and the receptacle may be removed independently from each other.

When the new exchange part is attached to the main body, the exchange part may move towards the receptacle parallel to a longitudinal axis of the receptacle during insertion, such that a needle of the exchange part may move towards a dispensing end of the receptacle. In particular, during an attachment of the exchange part, the needle may be pierced into the receptacle. If a receptacle is replaced in a state where an exchange part is attached to the main body, the receptacle may move towards the exchange part parallel to a longitudinal axis such that the receptacle may meet the needle. Thereby, the needle may be pierced into the receptacle.

According to a further aspect of the present disclosure, a method to transport material with the peristaltic pump as described above is disclosed. Preferably, the peristaltic pump is configured for being operated according to this method. The method comprises the step of successively actuating the piezoelements along the transport direction of the material and thereby squeezing the tube.

The peristaltic pump may comprise three piezoelements, which, in the further disclosure, are referred to as a first, a second and a third piezoelement for a better understanding of the embodiment and the transport mechanism. "First" means the first in a sequence, "second" the second in a sequence and "third" the third in a sequence of the three piezoelements in reference to the transport direction of the material. The first, second and third piezoelements may be arranged in a row along the transport direction. The first piezoelement may be closest to a receptacle, of all piezoelements.

The first, second and third piezoelements are representatives for the plurality of piezoelements. However, the number of the piezoelements is not limited. Furthermore, the peristaltic pump may comprise three levers, which may be referred to as a first, a second and a third lever. The first lever may be arranged such that the first piezoelement may actuate the first lever. The second piezoelement may actuate the second lever and the third piezoelement may actuate the third lever. The first lever may be configured to squeeze the tube in a first patch of the tube. The second lever may be configured to squeeze the tube in a second patch and the third lever may be configured to squeeze the tube in a third patch of the tube.

Preferably, when the first piezoelement is actuated and expands, the tube is squeezed in the first patch. Thereby, the tube may be closed. The material in the tube, for example insulin, which is positioned between the piezoelement and the tube guide, is displaced, preferably displaced towards a dispensing end of the tube. Thereby, an increased pressure is generated in the tube near the first patch of the tube. Thereby, the material may be moved forward in a transport direction. After that, the second piezoelement may be actuated, and the tube may be squeezed in the second patch and be closed. The material in the tube, which is positioned between the second lever and the tube guide, is displaced. An increased pressure occurs in the tube near the second patch, and the material is moved forward in the transport direction. Then, the third piezoelement may be actuated in a similar manner as the first and second piezoelements. At the same time when the third piezoelement is actuated, the first piezoelement may be discharged and may contract. Preferably, when the first piezoelement contracts, the diameter of the tube increases to its original, unsqueezed size. This may lead to a reduced inlet pressure in the tube, which may have the effect that material is drawn in from the receptacle. By the successive actuation of the piezoelements, material is transported from one end of the tube to the other end along the transport direction, so that the material from the receptacle can be dispensed, for example to a patient. Particularly, the squeezing of the tube may be achieved by levers, which are arranged between the tube and the piezoelement.

Preferably, the pump is operated such that at any time at least one of the piezoelements is actuated. Preferably, the actuated piezoelement squeezes the tube such that the tube is closed. Thereby, the piezoelement may function as a valve in order to inhibit that material can flow backwards in a direction opposite to the transport direction.

The term "medical fluid", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

```
H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39),
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2,
```

-continued

H-Asn-(Glu)5-des Pro36, Pro37, Pro38 [Asp28] Exendin-4(1-39)-(Lys)6-NH2,

H-(Lys)6-des Pro36 [Trp(O2)25, Asp28] Exendin-4(1-39)-Lys6-NH2,

H-des Asp28 Pro36, Pro37, Pro38 [Trp(O2)25] Exendin-4(1-39)-NH2,

H-(Lys)6-des Pro36, Pro37, Pro38 [Trp(O2)25, Asp28] Exendin-4(1-39)-NH2,

H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14, Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

wherein the group -Lys6-NH2 may be bound to the C-terminus of the Exendin-4 derivative;
or an Exendin-4 derivative of the sequence
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains.

The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Further features, refinements and expediencies become apparent from the following description of the exemplary embodiments in connection with the figures.

Like elements, elements of the same kind and identically acting elements are provided with the same reference numerals in the figures.

DETAILED DESCRIPTION

Figure 1:
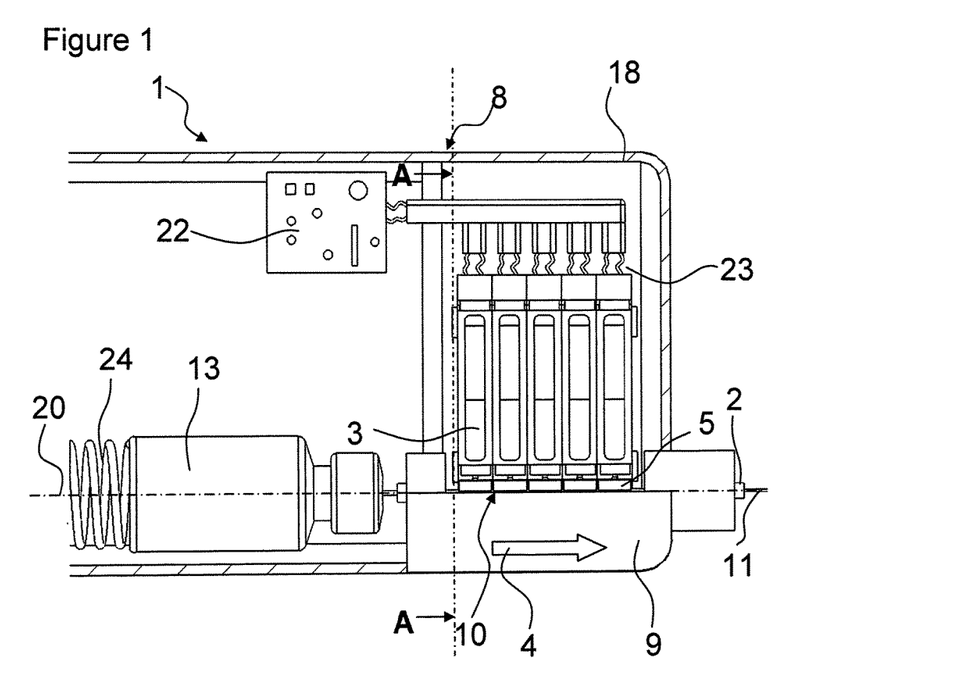
FIG. 1 shows a side view of an exemplary embodiment of a peristaltic pump with an exchange body being attached to a main body.

FIG. 1 shows a peristaltic pump 1, wherein a plurality of piezoelements 3 is arranged in a row along a tube 2. For clarity reasons, parts of a housing 18 of the pump 1 are cut away in this Figure. The peristaltic pump 1 may be configured to transport a material. The peristaltic pump 1 is particularly suitable for microfluidic applications. Particularly, the peristaltic pump 1 may be configured to dispense small amounts of fluids. The material to be transported is moved in the tube 2 along a transport direction 4. The material may be for example insulin. Preferably, the material may be a medical fluid. The movement of the material is caused by a successive expansion of the plurality of piezoelements 3. The piezoelements 3 are electrically connected to a power supply 22 by electric cables 23.

The tube 2 may be of an elastic material. Preferably, the tube 2 is arranged in a linear form such that it extends along an axis 20. The tube 2 runs linearly in a tube guide 10, which is integrated in an exchange part 9.

The exchange part 9 is configured such that it may be easily attached and detached to a main body 8 of the pump 1. In this illustration, the exchange part 9 is attached to the main body 8. The exchange part 9 provides an easy and fast way to substitute the elements of the peristaltic pump 1 which should be sterile before a use of the peristaltic pump 1, in particular a needle 11 and the tube 2. In particular, the exchange part 9 carries two needles 11, 12 (see FIG. 2), whereof one needle 12 (see FIG. 2) is configured to be inserted into a receptacle 13 and the other needle 11 is configured to dispense a material from the peristaltic pump 1.

The main body 8 comprises a housing 18 and the plurality of piezoelements 3. Furthermore, it may comprise at least one lever 5. The lever 5 may be arranged between the tube 2 and a piezoelement 3. The piezoelement 3 may move the lever 5 when it is actuated. The lever 5 may be configured to effect a squeezing of the tube 2. In a preferred embodiment, the pump 1 comprises a plurality of levers 5.

Furthermore, the receptacle 13 is located in the main body 8. It contains the material to be transported. In a preferred embodiment, the receptacle 13 may comprise a piston. The piston may be axially movable in the receptacle 13. A spring may exert a force on the piston to facilitate a movement of the piston. Thereby, no air pockets may occur in the receptacle 13 when material is drawn from the receptacle 13 into the tube 2.

In the condition shown in FIG. 1, the peristaltic pump 1 is ready to transport a material.

Figure 2:
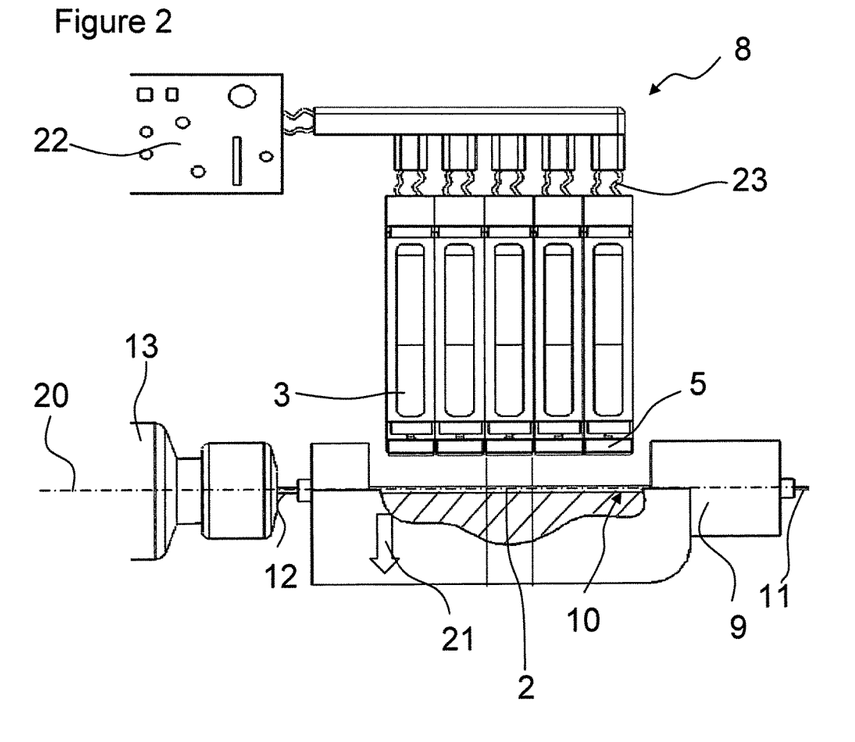
FIG. 2 shows a side view of the peristaltic pump of FIG. 1 with the exchange body being detached from the main body.

FIG. 2 shows the peristaltic pump 1 of FIG. 1, with the exchange part 9 being detached from the main body 8. The exchange part 9 carries the tube 2 and the needles 11, 12.

The exchange part 9 may be removed from the main part 8 in a moving direction 21. The moving direction 21 of the exchange part 9 may be perpendicular to the axis 20 of the tube 2.

In an exemplary embodiment, it may be possible to lock the exchange part 9 to the main body 8 by a flap. The flap may have to be opened in order to detach the exchange part 9 from the main body 8. The flap may close the main body 8 in order to inhibit that dust or other contaminants may invade into the pump 1.

Figure 3:
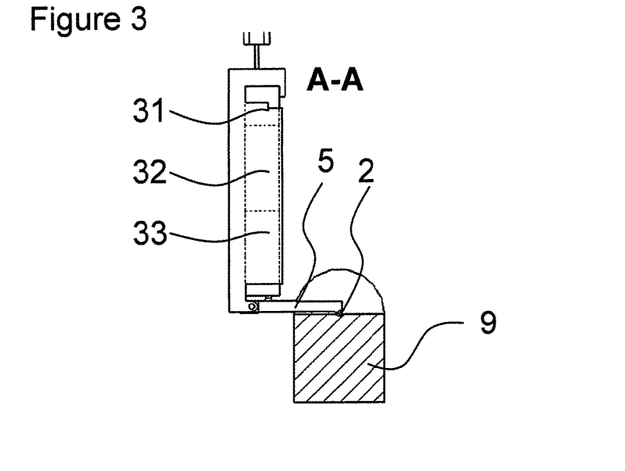
FIG. 3 shows a sectional view of parts of the peristaltic pump of FIG. 1.

FIG. 3 shows a sectional rear view of parts of the peristaltic pump 1 of FIG. 1. The section is cut along the line A-A as shown in FIG. 1. It shows how the lever 5 is arranged between the piezoelement 3 and the tube 2. In an exemplary embodiment of the pump 1, one piezoelement 3 may be composed of several smaller piezoelements (31, 32, 33).

Figure 4:
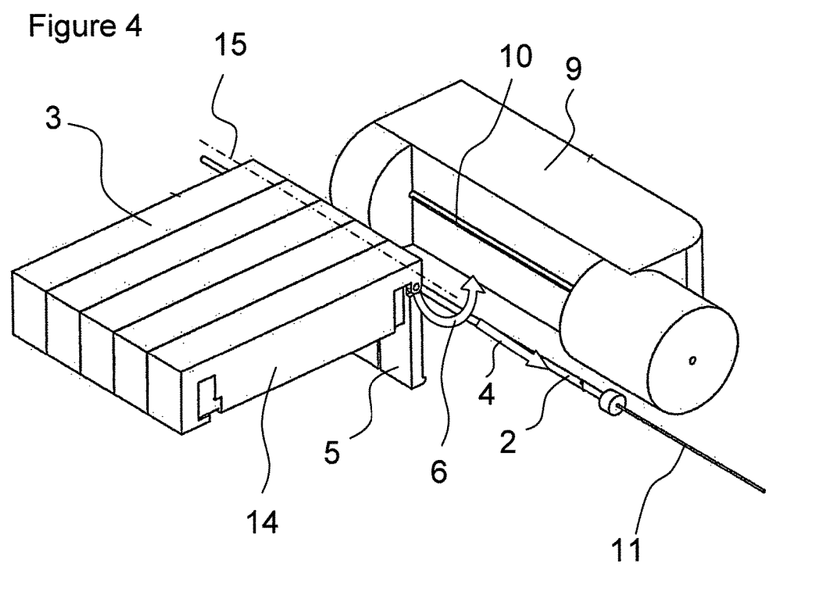
FIG. 4 shows an exploded view of parts of the peristaltic pump of FIG. 1.

FIG. 4 shows an exploded view of parts of the peristaltic pump 1 of FIG. 1. The plurality of piezoelements 3 is arranged in a holder 14. The tube is arranged in a tube guide 10, which is integrated in the exchange part 9. The tube guide 10 comprises a longitudinal groove, in which the tube 2 may run. The levers 5 are arranged in a row along the tube 2.

The expansion of a piezoelement 3 causes a movement 6 of at least one lever 5 around a rotation axis 15.

Preferably, one end of a piezoelement 3 is in contact with the holder 14 in a way such that the piezoelement 3 may expand only in a direction towards the tube 2, and the movement of the piezoelement 3 in the opposite direction is blocked by the holder 14. When actuated, the piezoelement 3 may expand in a direction such that the distance between the tube 2 and the moving end of the piezoelement 3 decreases.

Preferably, several piezoelements 3 are actuated at the same time. They may be expanded to a different size. For example, one piezoelement 3 may be expanded to its full size, while another piezoelement has just started to expand or started to contract.

Figure 5:
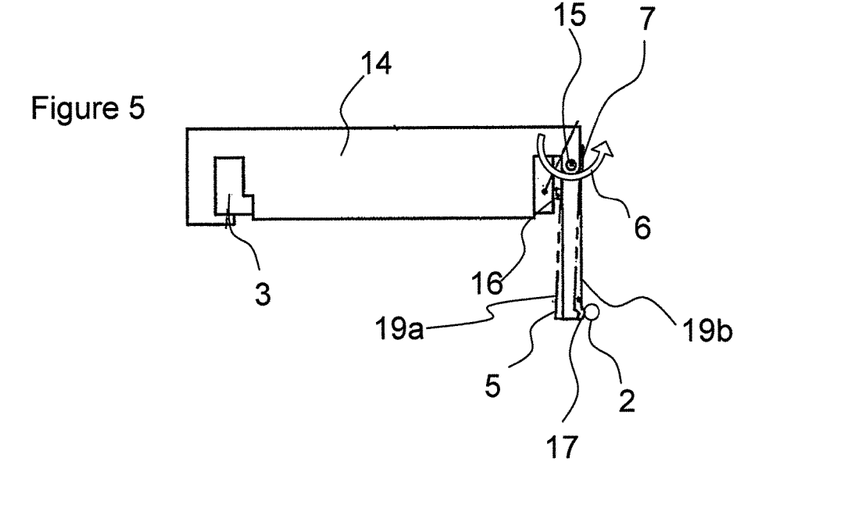
FIG. 5 shows a side view of a piezoelement and a lever mechanism of the peristaltic pump of FIG. 1.

FIG. 5 shows a side view of a piezoelement 3, a lever 5 and the tube 2. Here, the lever mechanism and the arrangement of the lever 5 between the piezoelement 3 and the tube 2 are shown in detail. The lever 5 may oscillate between two positions 19a and 19b. The position 19a occurs when the piezoelement 3 is contracted, and the lever 5 does not squeeze the tube 2. The lever 5 is in the position 19b when the piezoelement 3 is fully expanded. In position 19b the lever 5 closes the tube 2 by squeezing the tube 2.

The piezoelement 3 contacts the lever 5 in a contact area 16 of the lever 5. The contact area 16 may be configured as a protrusion on the lever 5. The lever 5 is in contact with the tube 2 in a patch 17 of the tube 2. When the piezoelement 3 expands, the lever 5 rotates in a rotational direction 6 around the rotation axis 15. The rotation axis 15 runs parallel to the axis 11 of the tube 2. The lever 5 is arranged in a way such that the piezoelement 3 meets the lever 5 in the contact area 16 of the lever 5 during its expansion. The lever 5 meets the tube 2 in the patch 17 of the tube 2 during its movement 6.

When the lever 5 is moved by the expansion of a piezoelement 3, it squeezes the tube 2 and thereby displaces the material in the tube 2.

When the piezoelement 3 contracts, the lever 5, which has been actuated by the piezoelement, starts to move in a direction opposite to the direction of movement 6 of the lever 5 when the piezoelement expands. Thereby the squeezing of the tube 2 by the lever 5 decreases, until the lever 5 no longer squeezes the tube 2. Thus the tube 2 can widen to its original, unsqueezed diameter.

The movement of the lever 5 in a direction opposite to the direction of movement 6 of the lever 5 when moved by the piezoelement 3 may be caused by an elasticity of the tube 2. When no force is applied on the tube 2 by the lever 5, the tube 2 may strive to widen and thereby move the lever 5. However, this may not be sufficient to move the lever 5 back to the position 19a. Thus, the movement of the lever 5 in a direction opposite to its direction of movement 6 when the piezoelement expands may be supported by a lever spring 7. The lever spring 7, which may be a flat spring, makes sure that the lever 5 is drawn back from the tube 2 after the contraction of a piezoelement 3. In a further embodiment, the lever spring 7 may be a different kind of spring, for example a spiral spring. The lever spring 7 pretensions the lever 5 in a direction that is opposed to the direction of movement 6 of the lever 5 which is caused by the expansion of the piezoelement 3.

Figure 6:
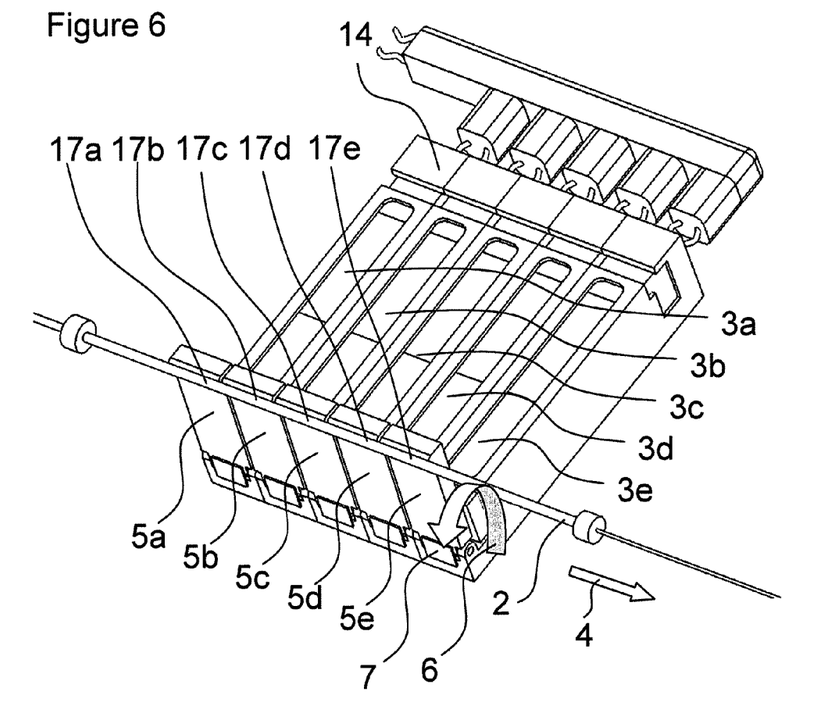
FIG. 6 shows the piezoelements and the lever mechanism of the pump of FIG. 1 from a perspective view.

FIG. 6 shows the piezoelements and the lever mechanism of the pump of FIG. 1 from a perspective view.

The pump comprises five piezoelements 3a to 3e.

However, the peristaltic pump 1 may also work with less than five piezoelements 3, for example with three piezoelements 3, or more than five piezoelements 3.

A first piezoelement 3a is first in the sequence of the piezoelements 3 in reference to the transport direction 4 of the material. In particular, the first piezoelement is located next to the receptacle 13. In particular, the first piezoelement 3a may be closest to the receptacle 13, compared to all other piezoelements 3. Analogically, the pump 1 comprises five levers 5a to 5e. The piezoelements 3 and the levers 5 are arranged such that each of the piezoelements 3a to 3e is configured to cause a movement of one of the levers 5a to 5e. The levers 5a to 5e may squeeze the tube 2 in patches 17a to 17e.

Preferably, the piezoelements 3 are successively actuated, such that the first piezoelement 3a is actuated firstly, the second piezoelement 3b is actuated secondly, the third piezoelement 3c is actuated thirdly and so forth. At a particular time, one of the piezoelements 3, for example the second piezoelement 3b, may be expanded by applying a voltage. At the same time, the third piezoelement 3c may already have started to expand, while the first piezoelement 3a may already have started to contract. Preferably, the piezoelements 3 may be driven by undulations, so that a regular material flow is generated.

FIGS. 7A to 7H illustrate successive steps of a successive squeezing of the tube 2 in the case of five piezoelements 3a to 3e acting on five levers 5a to 5e as shown in FIG. 6.

Figure 7A:
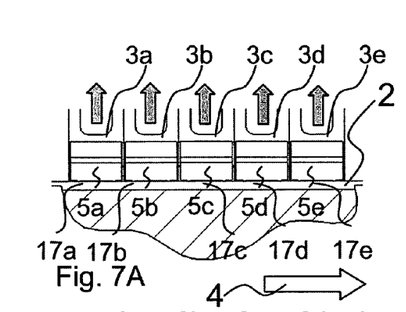
FIG. 7 shows different steps of the successive squeezing of the tube of FIG. 1 by the piezoelements.

In FIG. 7A, none of the piezoelements 3a to 3d is actuated, such that the tube 2 is not squeezed. The pump 1 is in a non operating state.

Figure 7B:
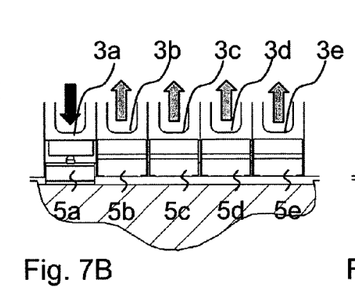

In FIG. 7B, the first piezoelement 3a is actuated and expands such that the first lever 5a is rotated and squeezes the tube 2 in a first patch 17a. Thereby, material is displaced from the squeezed patch 17a of the tube and transported forward in transport direction 4.

Figure 7C:
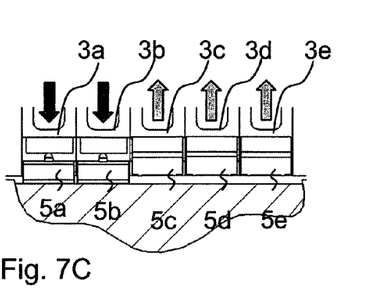

In FIG. 7C, the first piezoelement 3a and the second piezoelement 3b are expanded such that the first lever 5a and the second lever 5b squeeze the tube 2 in the first patch 17a and a second patch 17b. Thereby, material is displaced from the squeezed patches 17a, 17b and moved forward in transport direction 4.

Figure 7D:
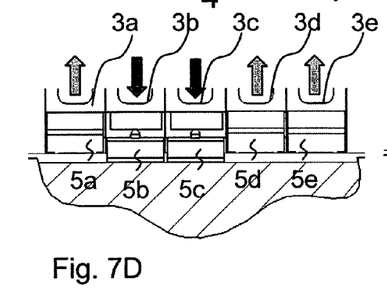
Figure 7E:
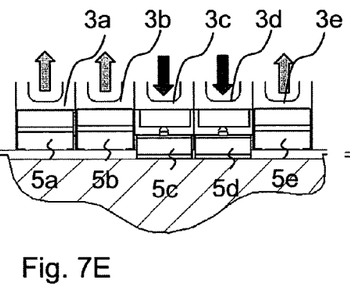
Figure 7F:
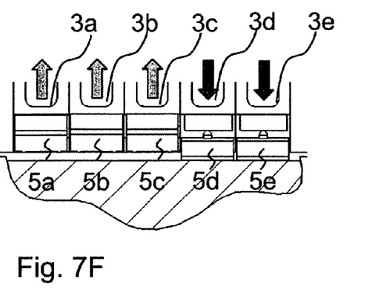
Figure 7G:
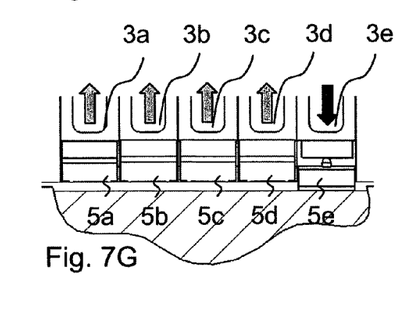

In FIG. 7D, the second piezoelement 3b and the third piezoelement 3c are expanded such that the second lever 5b and the third lever 5c squeeze the tube 2 in the second patch 17a and a third patch 17c. When the third piezoelement 3c is actuated and expands the first piezoelement 3a contracts.

When the first piezoelement 3a contracts and the first lever 5a is withdrawn from the tube 2, a widening of the tube 2 is enabled at the first patch 17a of the tube 2. The widening of the tube 2 caused by the contraction of the first piezoelement 3a may cause an inlet pressure, such that new material flows into the tube 2 from the receptacle 13.

As shown in the FIGS. 7E, 7F, 7G and 7H, the further piezoelements 3 are actuated in the same manner, such that a continuous transport of material is achieved.

Figure 7H:
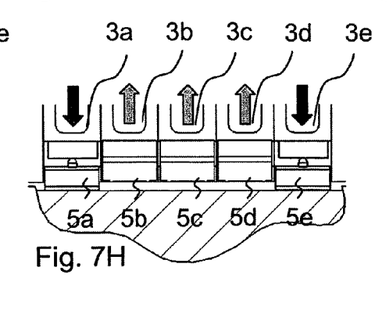

When all piezelements 5a to 5e have been successively actuated and the last piezoelement 3e is expanded, the first piezoelement 3a is actuated again as can be seen from FIG. 7H. After that the last piezoelement 3e contracts and the successive actuation continues with the steps shown in FIGS. 7C to 7H.

Preferably, the peristaltic pump 1 is operated such that at any time during the operation at least one lever 5 squeezes the tube 2 and closes it by that, so that the material always follows the transport direction 4 and no material can flow backwards. The succession of movement 6 of the levers 5 corresponds to the successive actuation of the piezoelements 3.

The invention claimed is:

1. A peristaltic pump, comprising:
a tube to transport a material in a transport direction;
a plurality of piezoelements arranged in a row along the tube, the plurality of piezoelements being configured to expand when they are actuated to cause a squeezing of the tube;
a holder having an expansion end and a blocking end, at least one of the plurality of piezoelements being held by the holder, the holder being configured to permit each held piezoelement to expand along an expansion direction toward the expansion end of the holder and configured to block movement of the piezoelement at the blocking end of the holder when the piezoelement is expanding; and
a plurality of levers, each lever being arranged between a corresponding at least one of the piezoelements and the tube, and each lever having a rotation axis located at a first end of the lever, a second end that is at an opposite longitudinal end of the lever from the first end, and a contact area being configured to interact with the corresponding at least one of the piezoelements, the contact area of the lever being closer to the rotation axis of the lever than to the second end of the lever;
wherein an expansion of the corresponding at least one of the piezoelements causes a tangential displacement of the corresponding contact area about the rotation axis of the lever, that in turn causes a movement of the lever; and
wherein each lever is configured to contact the tube at a location at the second end of the lever that is further from the rotation axis of the lever than the contact area is from the rotation axis of the lever.

2. The peristaltic pump of claim 1, further comprising a lever spring that is configured to pretension at least one of the levers in a direction that is opposed to a direction of movement of the lever caused by the expansion of at least one of the piezoelements.

3. The peristaltic pump of claim 1, further comprising a main body and an exchange part configured to be attachable to the main body.

4. The peristaltic pump of claim 3, wherein the exchange part comprises a tube guide for guiding the tube.

5. The peristaltic pump of claim 3, further comprising a receptacle containing the material to be transported, wherein the receptacle is located in the main body.

6. The peristaltic pump of claim 5, further comprising at least one needle that is configured to be inserted into the receptacle.

7. The peristaltic pump of claim 5, configured such that a contraction of at least one of the piezoelements causes an inlet pressure in the tube such that the material is drawn into the tube from the receptacle.

8. The peristaltic pump of claim 1, further comprising at least one needle.

9. The peristaltic pump of claim 1, wherein the peristaltic pump is configured to transport medical fluids.

10. The peristaltic pump of claim 1, wherein the tube is arranged in a linear form.

11. A method of transporting material with the peristaltic pump of claim 1, comprising the step of successively actuating the plurality of piezoelements along the transport direction of the material and thereby causing a squeezing of the tube by the plurality of levers along the transport direction.

12. The method of claim 11, wherein at any time during an operation of the pump at least one piezoelement of the plurality of piezoelements is actuated.

13. The peristaltic pump of claim 1, wherein at least one lever of the plurality of levers is rotationally coupled with the holder at the expansion end of the holder.

14. The peristaltic pump of claim 1, wherein each of the plurality of piezoelements is held by the holder.

15. The peristaltic pump of claim 1, wherein the holder is one of a plurality of holders, and wherein each of the plurality of piezoelements is held by a different holder selected from the plurality of holders.

16. The peristaltic pump of claim 1, wherein, for each lever, a longitudinal axis of the lever is oriented perpendicular to the expansion direction of the corresponding at least one of the piezoelements during at least some of the operation of the peristaltic pump.

17. The peristaltic pump of claim 1, wherein, for each of the plurality of piezoelements, the expansion direction of the piezoelement is substantially perpendicular to a longitudinal axis of the tube.

18. The peristaltic pump of claim 1, wherein, for each lever in the plurality of levers, the rotation axis of the lever is substantially parallel to a longitudinal axis of the tube.

19. A peristaltic pump, comprising:
a tube to transport a material in a transport direction;
a plurality of piezoelements arranged in a row along the tube, the plurality of piezoelements being configured to expand when they are actuated to cause a squeezing of the tube;
a holder having an expansion end and a blocking end, at least one of the plurality of piezoelements being held by the holder, the holder being configured to permit each held piezoelement to expand along an expansion direction toward the expansion end of the holder and configured to block movement of the piezoelement at the blocking end of the holder when the piezoelement is expanding; and
a plurality of levers, each lever being arranged between a corresponding at least one of the piezoelements and the tube with the corresponding at least one of the piezoelements acting on the lever via a contact position on the lever located proximal to a rotation axis such that expansion of the at least one of the piezoelements causes a tangential displacement of the contact position and consequently a rotation of the lever about the rotation axis, and each lever being configured to convert movement of at least one of the piezoelements into amplified movement against the tube with a distance between the rotation axis and a location on the lever where the lever moves against the tube being greater than a distance between the rotation axis and the contact position.

20. The peristaltic pump of claim 19, further comprising at least one lever spring that is configured to pretension at least one of the levers in a direction that is opposed to a direction of movement of the lever caused by the expansion of at least one of the piezoelements.

21. The peristaltic pump of claim 19, further comprising a main body and an exchange part configured to be attachable to the main body.

22. The peristaltic pump of claim 19, wherein the peristaltic pump is configured to transport medical fluids.

23. The peristaltic pump of claim 19, wherein at least one lever of the plurality of levers is rotationally coupled with the holder at the expansion end of the holder.

24. The peristaltic pump of claim 19, wherein each of the plurality of piezoelements is held by the holder.

25. The peristaltic pump of claim 19, wherein the holder is one of a plurality of holders, and wherein each of the plurality of piezoelements is held by a different holder selected from the plurality of holders.

26. The peristaltic pump of claim 19, wherein, for each lever, a longitudinal axis of the lever is oriented perpendicular to an expansion direction of the corresponding at least one of the piezoelements during at least some of the operation of the peristaltic pump.

27. The peristaltic pump of claim 19, wherein, for each of the plurality of piezoelements, an expansion direction of the piezoelement is substantially perpendicular to a longitudinal axis of the tube.

28. The peristaltic pump of claim 19, wherein, for each lever in the plurality of levers, the rotation axis of the lever is substantially parallel to a longitudinal axis of the tube.

* * * * *